United States Patent [19]
Longo

[11] Patent Number: 5,993,454
[45] Date of Patent: Nov. 30, 1999

[54] DRILL ATTACHMENT FOR A SURGICAL DRILL

[75] Inventor: Paul T. Longo, Kalamazoo, Mich.

[73] Assignee: Stryker Corporation, Kalamazoo, Mich.

[21] Appl. No.: 09/162,518

[22] Filed: Sep. 29, 1998

[51] Int. Cl.[6] .................................................. F16H 57/08
[52] U.S. Cl. .............................................. 606/80; 606/85
[58] Field of Search .................................. 606/80, 79, 85, 606/81, 180; 475/331, 343, 337; 173/213, 216

[56] References Cited

U.S. PATENT DOCUMENTS

| | | | |
|---|---|---|---|
| 3,598,188 | 8/1971 | Foster ....................................... | 173/165 |
| 3,669,199 | 6/1972 | Cullen et al. ............................ | 175/106 |
| 5,863,272 | 1/1999 | Anderson ................................. | 475/331 |

OTHER PUBLICATIONS

Stryker Instruments Blueprint, Handpiece Assembly Reamer Dec., 1990.
Stryker Instruments Blueprint, Hudson/Modified Trinkle Reamer Assembly, Apr., 1996.
Stryker Instruments Blueprint, Cordless Driver Handpiece Assembly, Jul., 1995.
Stryker Instruments Blueprint, System 4 Hudson/Modified Trinkle Reamer Attachment, Part No. 4103–235–010, Jul., 1998.
Stryker Instruments Blueprint, Rotary Handpiece Assembly, Part No. 4103–001–010, Aug., 1998.

*Primary Examiner*—Michael Buiz
*Assistant Examiner*—Vy Quang Bui
*Attorney, Agent, or Firm*—Flynn, Thiel, Boutell & Tanis, P.C.

[57] ABSTRACT

A drill attachment (10) for decreasing the rotational speed/increasing the output torque of a cutting accessory (14) that is attached to a drill such as a surgical drill (10). The drill attachment has an input drive shaft (34) that is coupled to the drive shaft (16) of the drill to rotate in unison with the drill drive shaft. The input drive shaft rotates a set of axially fixed input planet gears (58). The input planet gears rotate a ring gear (66) that is fitted around the input planet gears. The ring gear rotates a set of axially fixed output planet gears (70). The planet gears rotate an output drive shaft (84). By the selective dimensioning of the drive shaft and gears the output speed/torque can be reduced and increased as desired.

22 Claims, 4 Drawing Sheets

DRILL ATTACHMENT FOR A SURGICAL DRILL

FIELD OF THE INVENTION

This invention relates generally to powered surgical drills and, more particularly, to a speed reducing/torque increasing drill attachment for use with a powered surgical drill.

BACKGROUND OF THE INVENTION

In modern surgery, one of the most important instruments available to medical personnel is the powered surgical drill. Typically, this drill comprises a housing in which a motor is secured. The motor has a shaft that is connected to some type of chuck or other coupling assembly that is mounted to the housing. The coupling assembly holds a cutting accessory that is applied to the patient in order to perform a specific medical procedure. Some common cutting accessories are drill bits, burs and reamers. These accessories are used to drill into and/or separate sections of soft tissue and hard tissue, commonly referred to as bone. The ability to use surgical drills to actuate these and other cutting accessories has lessened the physical strain of physicians and other medical personnel that perform these medical procedures. Moreover, most surgical procedures can be performed more quickly and more accurately with powered surgical tools than with the manual equivalents that preceded them.

It is often desirable to increase the rotation force, the torque, developed by the motor internal to a surgical drill. Many drills are provided with internal gear assemblies that perform this function. Since an inevitable result of a gear assembly's increasing torque output is a decrease in rotational speed, these gear assemblies are referred to as speed reduction gear assemblies. Generally, the input-to-output speed reduction factor and the input-to-output torque amplification factor of these gear assemblies are identical. Moreover, manufacturers of surgical drills often provide removable drill attachments for coupling to drills that have their own speed reduction gear assemblies. The ability to selectively couple a drill attachment to a surgical tool makes it possible for a surgeon to even further increase the torque available to the cutting tool coupled to the drill. Often, these drill attachments are designed to reduce the speed/increase the torque by a pre-set whole number ratio. For example, drill attachments with internal gear assemblies that decrease speed of the motor drive shaft by 3:1 or 4:1 have been provided. (It should be understood that the above ratio refers to the relationship of the input shaft speed to the output shaft speed. The reciprocal of these ratios give the relationship between torque input and torque output.)

Often, planetary gear assemblies are used as speed reduction gear assemblies for both surgical drills and the removable drill attachments designed for use with these drills. A planetary gear assembly has a centrally located sun gear that is directly coupled to the drill drive shaft that provides the basic motive power. A set of gears, referred to as planet gears, are located around and engage the sun gear. A fixed ring surrounds the planetary gears. The inner surface of the ring has teeth which the planetary gears engage. The planet gears are connected to a common planet carrier. The planet carrier has a number of arms to which the individual planet gears are attached. When the sun gear is rotated, the sun gear transfers the rotational energy it receives to the planet gears. The planet gears, in turn, rotate both around their own axes and the axis of the sun gear. The rotation of the planet gears about the sun gear causes a like rotation of the planet carrier.

Planetary gear assemblies and other gear assemblies have proven to be useful assemblies for reducing the speed/ increasing the torque of the shafts connected to surgical drills. However, to date, it has been difficult to provide a removable drill attachment with a planetary gear assembly or other gear assembly that can be used to achieve a 2:1 speed reduction. This is because physically, owing to the relationships between the components of a conventional planetary gear assembly, it is impossible to dimension the components so that they cause an exact 2:1 speed reduction. The only way it is possible to form a conventional planetary gear assembly that achieves approximately a 2:1 speed reduction is to provide it with very small planet gears. Such an assembly would not be able to function for a long time at the high rotational speeds at which most surgical drills operate. Attempts to provide other gear assemblies that reduce rotational speed/increase torque by a factor of 2 have proven unsuccessful for use with surgical drills. While these other gear assembles provide the desired speed reduction/ increased torque, the direction of rotation of their output shafts is reversed from the direction input shaft rotation. It is impractical to provide removable drill attachments chucks with these gear assemblies since the change in rotation of the associated cutting accessory could be confusing to a surgeon in the middle of a surgical procedure.

SUMMARY OF THE INVENTION

This invention is related to a drill attachment gear assembly intended for use with a surgical drill for increasing the torque of the cutting accessory attached to the drill. The gear assembly of this invention can be used to obtain a 2:1 reduction of motor speed wherein the output force is both centered around the axis around which the input force is applied and in the same direction as the direction of the input force.

BRIEF DESCRIPTION OF THE DRAWINGS

The invention is pointed out with particularity in the claims. The above and further features of the invention may be better understood by reference to the following description taken in conjunction with the accompanying drawings in which:

DETAILED DESCRIPTION

Figure 1:
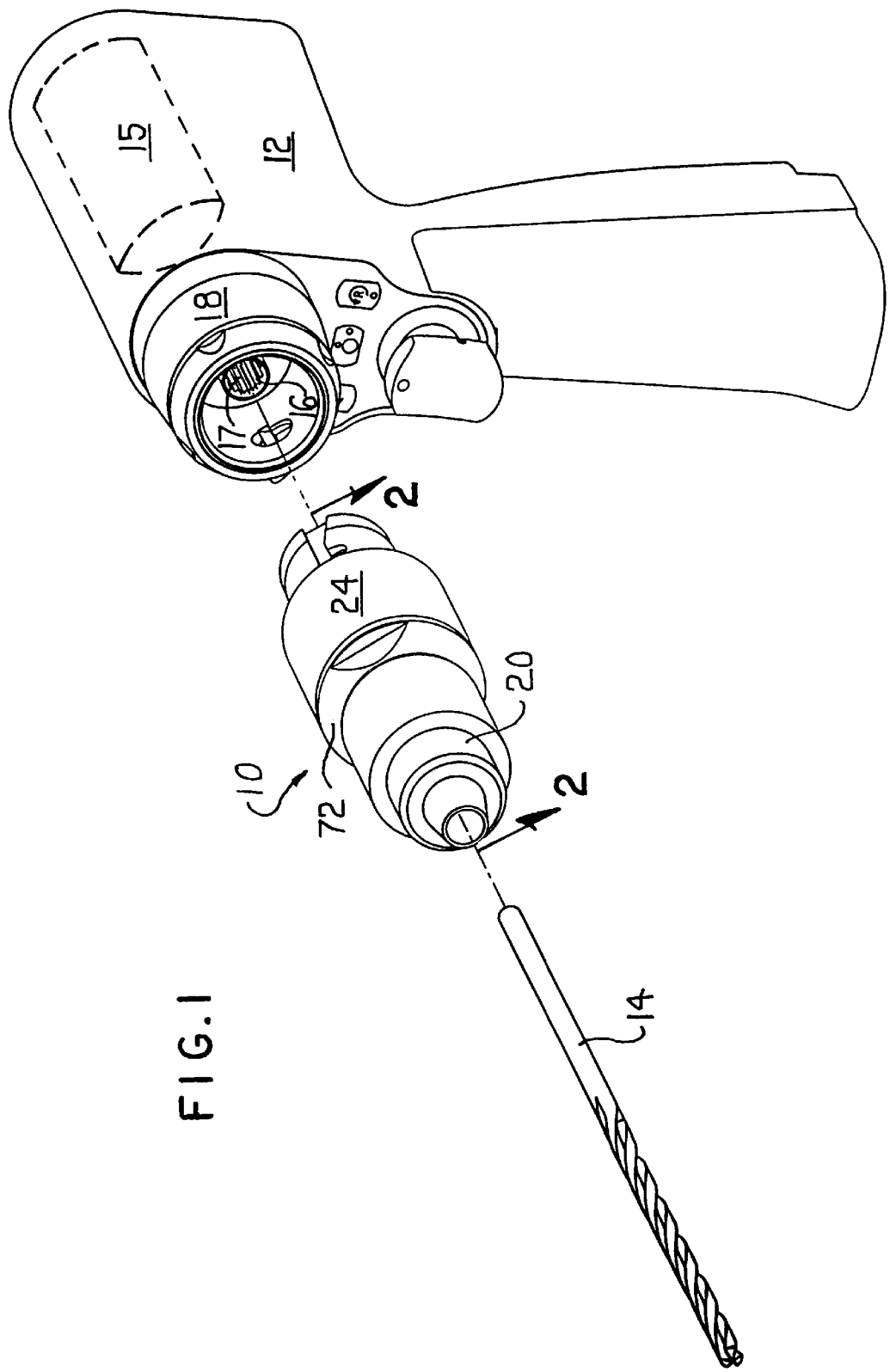
FIG. 1 is a perspective view illustrating how a drill attachment of this invention is used to transfer power from a surgical drill to a cutting accessory.

FIG. 1 depicts a drill attachment 10 of this invention and how the attachment used to transfer rotational power developed by a drill 12 to a cutting accessory 14. More specifically, drill 12 is a surgical drill such as the High Torque One-Quarter Inch Jacobs Drill, marketed by Stryker Corporation of Kalamazoo, Mich. as Part No. 4103-180. A motor 15 (represented by a phantom block) internal to drill 12 rotates a shaft 16 that extends out of the drill. In some versions of the invention the motor 15 turns at a rate of between 10,000 to 30,000 RPM. A gear train internal to the drill 12 (gear train not illustrated) transfers the power developed by the motor 15 to the shaft 16 so that the shaft has a maximum rotational speed of between 900 to 2,000 RPM.

The drill attachment 10 is coupled to the front end of the drill 12 so as to seat in a collar 18 integral with the front of the drill. A gear assembly internal to the drill attachment 10, described and illustrated hereinafter, transfers the rotational power developed by shaft 16 to a chuck 20 mounted to the front of the drill attachment. Chuck 20 is used to hold the cutting accessory 14. In the depicted version of the invention, the cutting accessory 14 is a drill bit. Still another cutting accessory used with drill attachment 10 is a reamer.

The drill attachment 10 of this invention is now described in detail by reference to FIGS. 2–5. Drill attachment 10, includes an input housing 24 which contains most of the components of the attachment. Input Housing 24 is formed to have a narrow diameter stem section 26. Stem section 26 is the portion of the housing 24 that is inserted into the collar 18 of the drill 12. The outer surface of stem 26 is formed with grooves 28 designed to receive an axial retention leaf spring latch 25 that holds the drill attachment 10 to the drill and an anti-rotation key that stops movement of the attachment, (key not illustrated). Input housing 24 is further formed to have a head 30 that is integral with and extends coaxially forward from stem 26. In the depicted version of the invention, head 30 has an outer diameter greater than that of stem 26. A multi-section bore 32 extends through input housing 24 from the end of the stem 26 coupled to drill 12 to the front end of the head 30.

An input drive shaft 34 is rotatably mounted in the portion of housing bore 32 that extends from the open end of the housing stem 26 to the portion of the head 30 adjacent the stem. Two spaced apart bearing assemblies 38 rotatably couple input drive shaft 34 to input housing 24. The bearing assemblies 38 are located in the portion of housing bore 32 that extends through stem 26. Axial movement of the bearing assemblies 38 is blocked, in part, by two C-rings 40, one located adjacent each bearing assembly. Each C-ring 40 is seated in an annular groove 42 formed in the outer wall of the drive shaft 34 adjacent the section of the shaft 34 over which the associated bearing assembly 38 is located. A retaining ring 44 prevents the bearing assembly 38 closest the open end of stem 26 from movement out of the housing bore 32. Retaining ring 44 is seated in a groove 46 formed in the inner wall of input housing 24 that defines bore 32 so that the ring abuts the adjacent bearing assembly. The forward-directed end of the second bearing assembly 38, the bearing assembly located proximal to the chuck 20, abuts a fixed planet carrier 48.

The input drive shaft 34 is formed with a bore 36 that extends axially through the drive shaft. Drive shaft 34 is further formed to have an end 49 closest to drill 12 that is shaped to have a polygonal shaped outer surface. When the drill attachment 10 is coupled to a drill 12, the drive shaft end 49 seats in complementary-profiled opening 17 formed in the head of drill shaft 16. Consequently, the rotation of drill shaft 16 causes a like rotation of input drive shaft 34.

Input drive shaft 34 is formed to have a head provided with gear teeth that form an input sun gear 52. The input drive shaft 34 also has a nose section 54 located forward of the input sun gear 52. The outer diameter of nose section 54 is less than the outer diameter of the input sun gear 52.

The input sun gear 52 engages three input planet gears 58 that are rotatably mounted to the input housing 24. More specifically, the input planet gears 58, which are equiangularly spaced around the longitudinal axis of input drive shaft 34, are mounted to the planet carrier 48. The planet carrier 48 is ring-shaped and located around input drive shaft 34. Planet carrier 48 is press fit in a stepped section of housing bore 32 located in the portion of the head 30 of the housing adjacent stem 26. In the depicted version of the invention, the forward and rear outer edges of planet carrier 48 are formed with inwardly directed steps 61 to facilitate the mounting of the carrier in input housing 24. Each of the input planet gears 58 is rotatably mounted to fixed axle pin 64. Axle pins 64 are press fit in bores 65 that extend through planet carrier 48.

A circularly shaped ring gear 66 surrounds the input planet gears 58. Ring gear 66 has an inner surface with teeth 68 that engage input planet gears 58. The outer wall of ring gear 66 is smooth. Ring gear 66 is further designed so that its outer diameter is less than the diameter of the adjacent inner wall of input housing 24 that defines the section of the housing bore 32 in which the ring gear is seated. Thus, there is a small interstitial space between the outer wall of the ring gear 66 and the adjacent inner wall of the input housing 24. In some versions of this invention, the gap between the inner wall of the input housing 24 and the outer wall of the ring gear 22 is approximately between 0.007 and 0.011 inches (0.18 and 0.28 mm). Thus, ring gear 66 "floats" relative to input housing 24.

The gear assembly of this invention includes a second set of planet gears, output planet gears 70, that also engage ring gear 66. The output planet gears 70 are fitted to an output housing 72 that is mounted in and extends forward from the open end of input housing head 30. The output housing 72 is a generally ring shaped structure with a bore 74 that extends axially through it. Output housing bore 74 extends coaxially with input housing bore 32. The rear end of output housing 72 is seated in the front end of the input housing bore 32. The outer surface of the middle section of output housing 72 is provided with threading 76. The threading 76 engages threading 78 provided around the inner wall of input housing 24. The output housing 72 is further formed to have an outwardly extending annular lip 73 located forward of the surface on which threading 76 is formed. Lip 73 extends over the open forward end of input housing 24 to limit the extent to which the output housing 72 is seated in input housing bore 32.

The output planet gears 70 are seated against the rearwardly directed face of output housing 72. The output planet gears 70 are rotatably mounted over fixed axle pins 81. The axle pins 81 are press fit into bores, (not identified,) that extend into the output housing 72 from the rearwardly directed face of the housing 72. It will be further noted that, within the ring gear 66, two ring-shaped washers 82 are located between input and output planet gears 58 and 70, respectively. Washers 82 are provided to prevent the output planet gears 70 from separating from the output housing 72.

An output drive shaft 84 is located in output housing bore 74. The output drive shaft 84 has an elongated stem section 86 that extends out of the front end of the output housing 72. Two bearing assemblies 88 that extend between the inner wall of the output housing 72 that defines bore 74 and the stem section 86 rotatably mount the output drive shaft 84 in the output housing 72. The rear face of the rearward of the two bearing assemblies 88 abuts an inwardly directed step 90 internal to output housing 72. A retaining ring 92 prevents the bearings from coming out of the front end of output housing bore 74. The outer perimeter of retaining ring 92 is seated in an annular groove 96 formed in the inner wall of output housing 72 that defines bore 74. Two washers 97 are located between the front face of the forwardmost bearing assembly 88 and the adjacent surface of chuck 20.

The output drive shaft 84 has a toothed head that functions as an output sun gear 98. Output sun gear 98 is shaped to have a diameter greater than that of the stem 86 with which it is integrally formed. Owing to its large diameter, output sun gear 98 blocks outward movement of the input planet gears 58 so as to prevent the input planet gears from coming out of the planet carrier 48.

It will also be noted that, in the illustrated version of the invention, output drive shaft 84 has a bore 102 that extends axially through the shaft. From FIG. 2 it can be seen that the nose section 54 of input drive shaft 34 extends into the adjacent open end of bore 102 of output drive shaft 84. A flexible quad ring 104 is seated in an annular groove 106 formed contiguously with bore 102 inside output drive shaft 84. Quad ring is fitted over the portion of the nose section 54 that extends into bore 102. The quad ring 104 provides a barrier to prevent lubricating material disposed inside the gear assembly from flowing outside the drill attachment 10 along the inner walls of either the input drive shaft 34 or the output drive shaft 84.

The output drive shaft 84 engages chuck 20. Internal to the chuck are jaws that hold the cutting accessory 14 in place. (The jaws and other components internal to the chuck 20 are not illustrated.) On type of chuck 20 integral with drill attachment 10 is a "Jacobs" chuck. The jaws rotate in unison with the output drive shaft 84 so as to cause a like movement of the cutting accessory 14.

When the drill 12 is actuated, the rotation of socket 16 causes the input drive shaft 34 to rotate. The movement of the input drive shaft 34 and the input sun gear 52 integral therewith causes the input planet gears 58 to rotate around their axes. The rotation of the input planet gears 58 causes the ring gear 66, which is not fixed, to rotate. Actuation of the ring gear 66, in turn, forces the output planet gears 70 to rotate around their axes. The movement of the output planet gears 70 forces the rotation of the output sun gear 98 and output drive shaft 84. The rotation of the output drive shaft causes the like movement of the cutting accessory 14 coupled to it by the chuck 20.

An advantage of the drill attachment 10 of this invention is that the input and output drive shafts 34 and 84, respectively, can be shaped so that the output sun gear 98 has twice as many teeth as the input sun gear 52. When these gears are so dimensioned, and assuming the input and output planet gears have a common pitch, there is a 2:1 reduction in the rotational speed of the output drive shaft 84 relative to the input drive shaft 34. Consequently, there is 1:2 increase in torque available at the output drive shaft 84 relative to what is available at the input drive shaft 34. Since the drive shafts rotate in the same direction, this speed reduction/torque increase is accomplished without having to reverse the direction at which the cutting accessory 14 rotates relative to the shaft 16 of the drill 12.

Still another advantage of the drill attachment 10 of this invention is that it is relatively compact in size. For example, in some preferred versions of this invention, the drill attachment has a maximum overall length of 4.5 inches (11.4 cm) and the diameter of the largest component, the input housing, is no greater than 1.4 inches (3.6 cm). Accordingly, this drill attachment 10, when fitted to a drill 12, does not appreciable block the field-of-view of the surgeon using the drill.

Thus, the drill attachment of this invention can be used to effect a 2:1 speed reduction of the output speed of drill shaft while keeping the rotational direction of the output shaft 84 constant with that of the drill shaft 16 and does not noticeably obstruct the view of persons' using it.

Moreover, additional advantages are gained in many preferred versions of this invention in which the ring gear 66 floats relative to the adjacent wall of the input housing 24 in which it is seated. A first one of these advantages is that this float eliminates the need to provide a bearing assembly in order to have a low-friction interface between the ring gear and the adjacent wall of the housing. Still another advantage of this construction of the invention is that it provides the drill attachment 10 with radial compliance that accommodates tolerancing ranges in manufacturing of the gears and their assembly into the drill attachment.

It should be recognized that the foregoing description is directed to specific embodiment of this invention and that other embodiments of this invention may vary from what has been described. For example, there is no requirement that, in each version of this drill attachment, the input and output drive shafts always be dimensioned to cause a 2:1 reduction between input and output rotational speeds. In other versions of this invention, the drive shafts 34 and 84 can be dimensioned to cause the output drive shaft to spin faster than the input drive shaft. Moreover, the components from which the drill attachment are assembled may vary from what has been described. For example, in some versions of the invention the input planet gears may be directly mounted to the housing in which the planet gears are contained. Still other versions of this invention may have a single housing.

Also, in the described version of the invention, the teeth 68 of the ring gear 66 extend the length of the ring gear. Different sections of each tooth 68 engages both the input planet gears 58 and the output planet gears 70. In still other versions of the invention, ring gear may be provided with two sets of teeth wherein one set of teeth circumscribe a circle having a different diameter than the circle circumscribed by the second set. The two sets of teeth of this ring may have the same pitch or different pitches. Alternatively, the ring of this invention may be provided with two sets of teeth that circumscribe a common diameter, but have different pitches. Clearly, in these versions of the invention, one set teeth would engage the input planet gears while the second set of teeth engage the output planet gears. Such constructions may be desirable to accomplish other changes in speed/torque settings.

Figure 2:
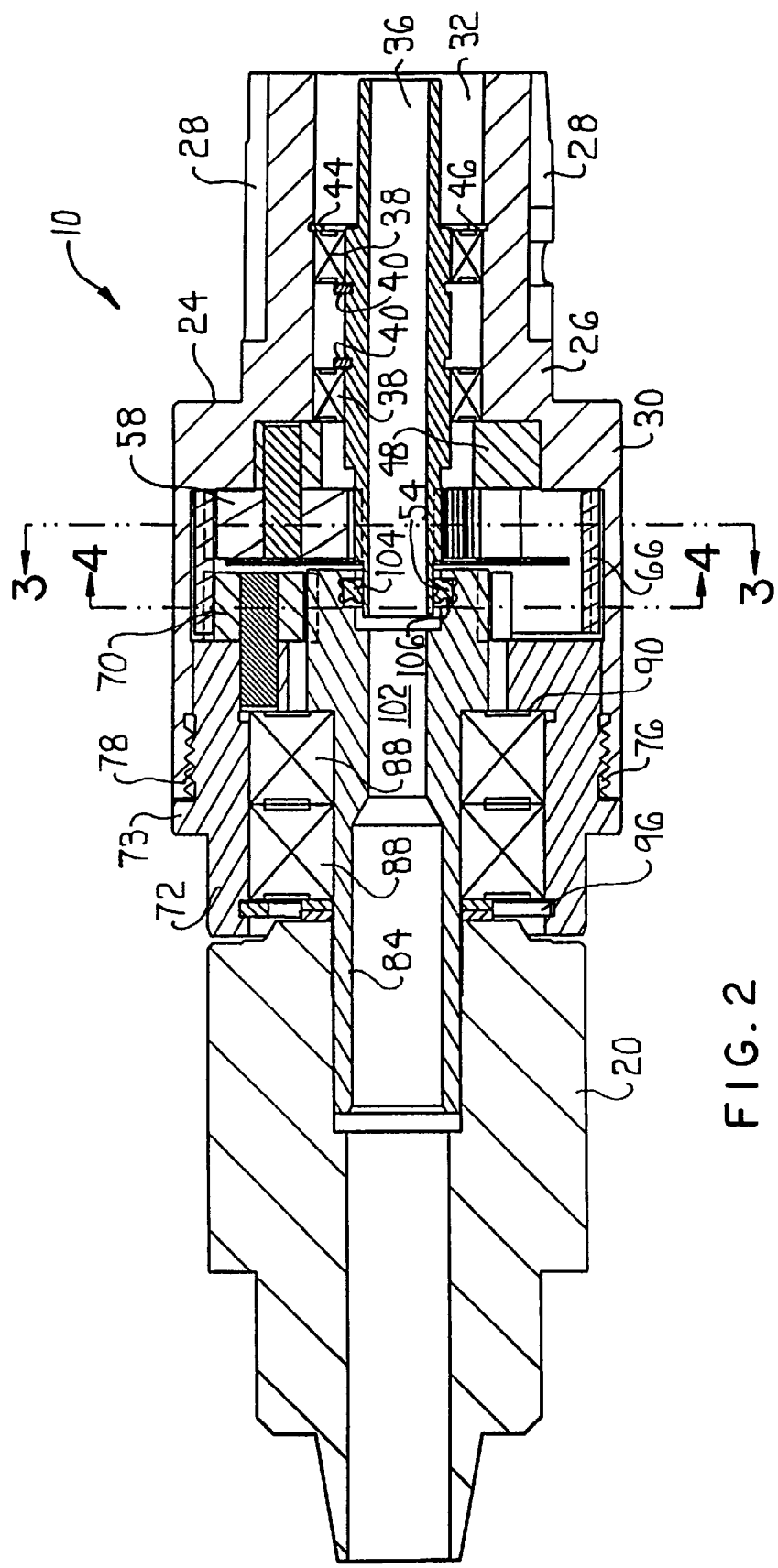
FIG. 2 is a longitudinal cross sectional view of the drill attachment taken along line 2—2 of FIG. 1.
Figure 3:
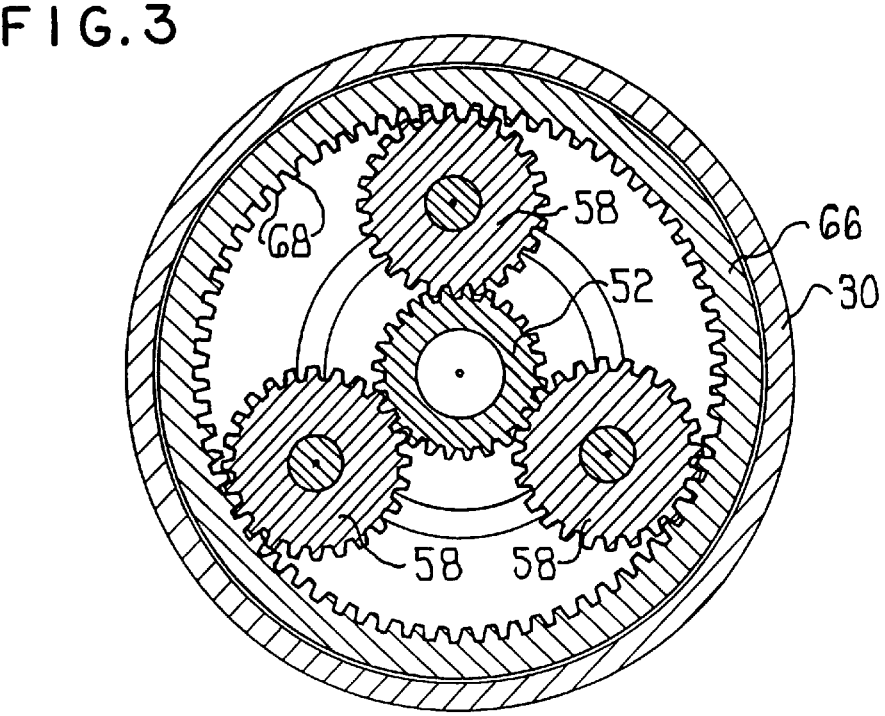
FIG. 3 is a lateral cross sectional view of the input gear train taken along line 3—3 of FIG. 2.
Figure 4:
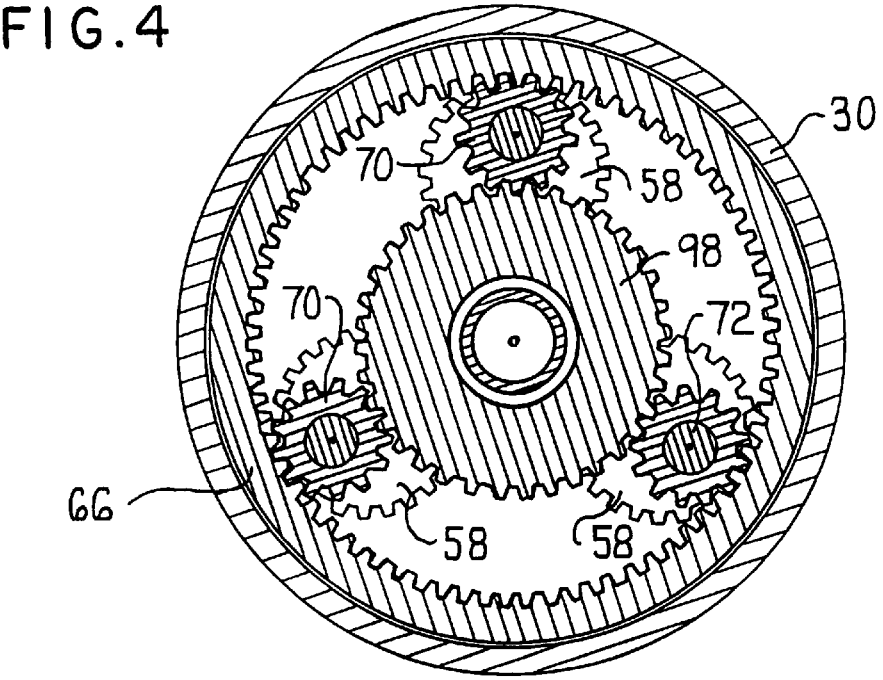
FIG. 4 is a lateral cross sectional view of the output gear assembly taken along line 4—4 of FIG. 2.
Figure 5:
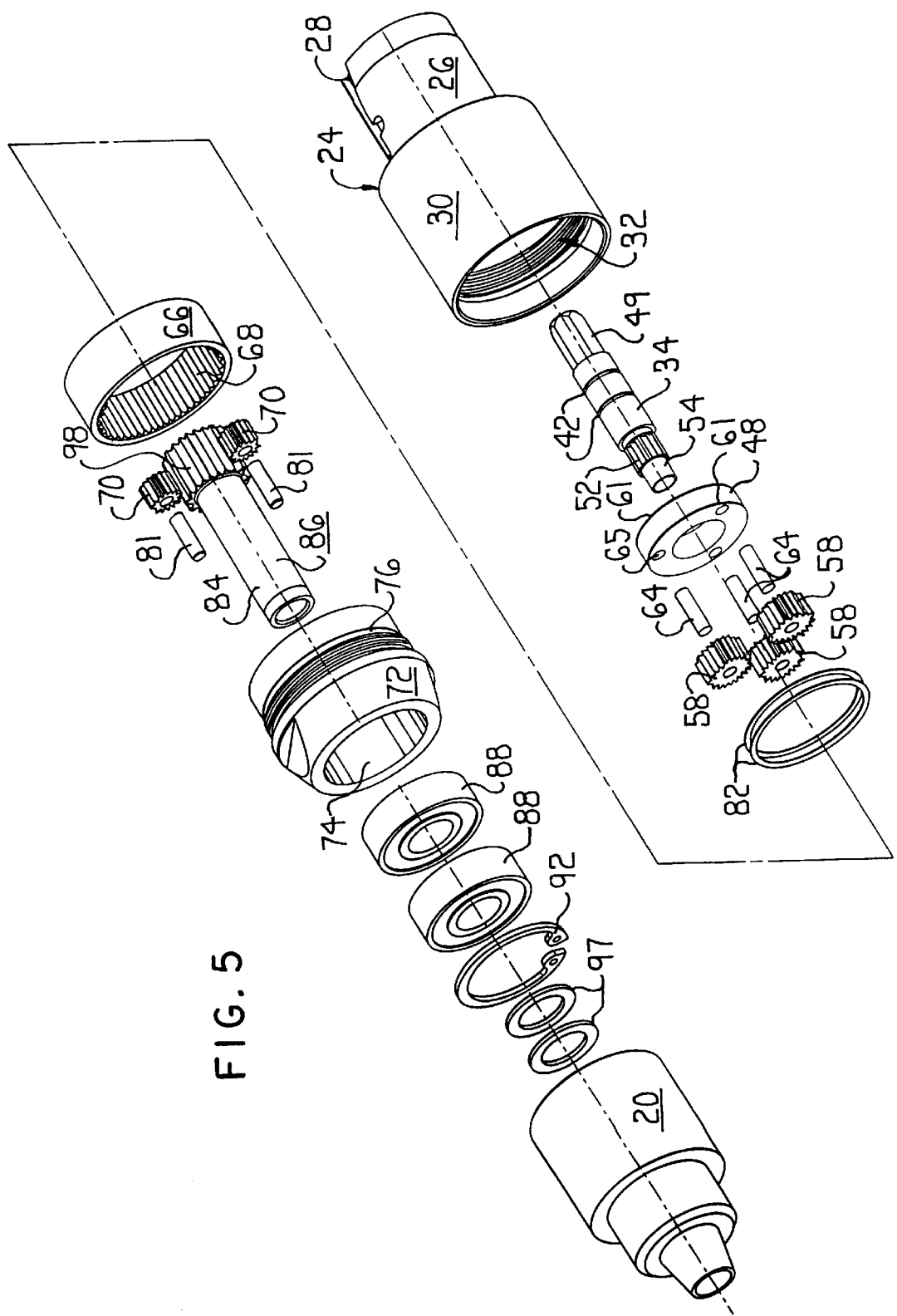
FIG. 5 is an exploded view of the drill attachment.

Also, there is no requirement that the axes along which the input and output planet gears 58 and 70, respectively, rotate lie along a common radial line that extends outward from the center of the drill attachment 10. While this alignment is depicted in FIG. 2, it is not required in all versions of this invention. Moreover, there need not always be a 1:1 ratio in the number of input planet gears to the number of output planet gears.

Also, only one particular type of coupling assembly was shown in association with the drill for holding a complementary cutting accessory. Clearly, other coupling assemblies may be used with this attachment.

It should likewise be recognized that, in some versions of this invention the drill attachment 10 may be permanently fitted to the drill 12 with which it is used. Also, the term drill should be understood to encompass other forms of surgical tools such as burs and wire drivers.

Therefore, it is the object of the appended claims to cover all such modifications that lie within the true spirit and scope of this invention.

The embodiments of the invention in which an exclusive property or privilege is claimed are defined as follows:

1. A drill attachment comprising:
   a housing having first and second opposed ends, said housing first end having a means for releasably coupling said housing to a drill;

an input drive shaft rotatably coupled to said housing, said input drive shaft having a first end located adjacent said housing first end and a second end distal from said first end, said first end having a coupling mechanism for mating said input drive shaft to a drill shaft, said second end shaped to form an input sun gear;

a plurality of input planet gears that are rotatably mounted to a plurality of first axial pins that are fixedly fitted to said housing, said input planet gears being positioned to engage said input sun gear so as to rotate with the rotation of said input drive shaft;

a ring gear rotatably disposed in said housing and fitted around said input planet gears, said ring gear having an outer surface and an inner surface, said inner surface being formed with teeth for engaging said input planet gears so that said ring gear rotates with the rotation of said input planet gears;

a plurality of output planet gears that are rotatably mounted to a plurality of second axial pins that are fixedly fitted to said housing, said output planet gears being positioned to engage said teeth of said ring gear so that said output planet gears rotate with said rotation of said ring gear;

an output drive shaft rotatably coupled to said housing, said output drive shaft having first and second spaced apart ends, said output drive shaft first end having an output sun gear positioned to engage said output planet gears so that said output drive shaft rotates with the rotation of said output planet gears, said output drive shaft second end being located adjacent said housing second end; and a coupling assembly fitted to said output drive shaft second end for releasably coupling a cutting accessory to said output drive shaft so that the cutting accessory rotates in unison with said output drive shaft.

2. The drill attachment of claim 1, wherein said input sun gear, said input planet gears, said output planet gears and said output sun gear are dimensioned so that when said input drive shaft is rotated there is a 2:1 speed reduction between rotational speed of said input drive shaft and rotational speed of said output drive shaft.

3. The drill attachment of claim 1, wherein said input planet gears are rotatably mounted to a carrier that is fixedly mounted in said housing.

4. The drill attachment of claim 1, wherein said housing and said ring gear are dimensioned so that said outer surface of said ring gear is spaced away from an adjacent inner wall of said housing that defines a space in which said ring gear is seated.

5. The drill attachment of claim 1, wherein:
said output drive shaft has an axially extending bore that opens towards said input sun gear;
said input drive shaft is formed with a nose that extends forward of said input sun gear into said output drive shaft bore; and
a flexible ring is fitted over said nose of said input drive shaft and extends between said nose and an inner wall of said output drive shaft that defines said output drive shaft bore.

6. The drill attachment of claim 1, wherein: said housing is a multi-part assembly having an input housing and output housing; said input drive shaft is rotatably mounted in said input housing; and said output drive shaft is rotatably mounted to said output housing.

7. The drill attachment of claim 6, wherein said input planet gears are rotatably mounted to said input housing and said output planet gears are rotatably mounted to said output housing.

8. The drill attachment of claim 1, wherein said ring gear has a single set of teeth and both said input planet gears and said output planet gears engage the single set of teeth of said ring gear.

9. A surgical drill assembly comprising:
a surgical drill, said surgical drill including: a handpiece; a motor disposed in said handpiece; and a drill shaft rotatably mounted in said handpiece and connected to said motor to rotate with actuation of said motor; and
a drill attachment, said drill attachment including
a housing that is coupled to said handpiece of said surgical drill and locked against rotation relative to said surgical drill;
an input drive shaft rotatably mounted in said housing, said input drive shaft having a first end located adjacent said housing first end and a second end distal from said first end, said first end being coupled to said drill shaft, said second end having a head shaped to form an input sun gear;
a plurality of input planet gears that are rotatably mounted to a plurality of first pins that are fixedly fitted to said housing, said input planet gears being positioned to engage said input sun gear so as to rotate with the rotation of said input drive shaft;
a ring gear rotatably disposed in said housing and fitted around said input planet gears, said ring gear having an outer surface and an inner surface, said inner surface being formed with teeth for engaging said input planet gears so that said ring gear rotates with the rotation of said input planet gears;
a plurality of output planet gears that are rotatably mounted to a plurality of second pins that are fixedly fitted to said housing, said input planet gears being positioned to engage said teeth of said ring gear so that said output planet gears rotate with said rotation of said ring gear;
an output drive shaft rotatably coupled to said housing, said output drive shaft having first and second spaced apart ends, said output drive shaft first end having an output sun gear positioned to engage said output planet gears so that said output drive shaft rotates with the rotation of said output planet gears, said output drive shaft second end being located adjacent said housing second end; and
a coupling assembly coupled to said output drive shaft second end for releasably coupling a cutting accessory to said output drive shaft so that the cutting accessory rotates in unison with said output drive shaft.

10. The surgical drill of claim 9, wherein said drill attachment housing is configured to be removably couplable to said handpiece and said drill attachment input drive shaft is configured to be removably couplable to said drill shaft.

11. The surgical drill of claim 9, wherein said input sun gear, said input planet gears, said output planet gears and said output sun gear are dimensioned so that when said input drive shaft is rotated there is a 2:1 speed reduction between rotational speed of said input drive shaft and rotational speed of said output drive shaft.

12. The surgical drill of claim 9, wherein said input planet gears are rotatably mounted to a carrier that is fixedly mounted in said drill attachment housing.

13. The surgical drill of claim 9, wherein said drill attachment housing and said ring gear are dimensioned so that said outer surface of said ring gear is spaced away from an adjacent inner wall of said housing that defines a space in which said ring gear is seated.

14. The surgical drill of claim 9, wherein:
   said output drive shaft has an axially extending bore that opens towards said input sun gear;
   said input drive shaft is formed with a nose that extends forward of said input sun gear into said output drive shaft bore; and
   a flexible ring is fitted over said nose of said input drive shaft and extends between said nose and an inner wall of said output drive shaft that defines said output drive shaft bore.

15. The surgical drill of claim 9, wherein: said drill attachment housing is a multi-part assembly having an input housing and output housing; said input drive shaft is rotatably mounted in said input housing; and said output drive shaft is rotatably mounted to said output housing.

16. The surgical drill of claim 9, wherein said ring gear has a single set of teeth and both said input planet gears and said output planet gears engage the single set of teeth of said ring gear.

17. A drill accessory for attachment to a surgical drill, said drill accessory including:
   a housing have opposed first and second ends, said first end having a means for coupling said housing to a surgical drill;
   an input drive shaft rotatably mounted in said housing first end, said input drive shaft having a means for coupling said input drive shaft to a drill shaft integral with the surgical drill and being formed with an input sun gear that is coaxial with said input drive shaft and that is located within said housing;
   an output drive shaft rotatably mounted in said housing second end, said output drive shaft being coaxially aligned with said input drive shaft and being formed with an output sun gear that is coaxial with said output drive shaft and that is located adjacent said input sun gear;
   a ring gear disposed in said housing, said ring gear having an outer wall that is dimensioned to be spaced away from an adjacent inner wall of said housing so that said ring gear can freely rotate in said housing and an inner wall formed with teeth, said ring gear being positioned to extend around portions of said sun gears that are adjacent each other;
   a plurality of input planet gears that are rotatably mounted in said housing to first pins that are fixed to said housing, said input planet gears being positioned to engage said input sun gear and said teeth of said ring gear so that said input planet gears transfer the rotational movement of said input drive shaft to said ring gear;
   a plurality of output planet gears that are rotatably mounted in said housing to second pins that are fixed to said housing, said output planet gears being positioned to engage the teeth of said ring gear and said output sun gear so that rotation of said output planet gears transfers the rotational movement of said ring gear to said output drive shaft; and
   a coupling assembly attached to said output drive shaft second end for releasably coupling a cutting accessory to said output drive shaft so that the cutting accessory rotates in unison with said output drive shaft.

18. The drill attachment of claim 17, wherein said input sun gear, said input planet gears, said output planet gears and said output sun gear are dimensioned so that when said input drive shaft is rotated there is a 2:1 speed reduction between rotational speed of said input drive shaft and rotational speed of said output drive shaft.

19. The drill attachment of claim 17, wherein said input planet gears are rotatably mounted to a carrier that is fixedly mounted in said housing.

20. The drill attachment of claim 17, wherein:
   said output drive shaft has an axially extending bore that opens towards said input sun gear;
   said input drive shaft is formed with a nose that extends forward of said input sun gear into said output drive shaft bore; and
   a flexible ring is fitted over said nose of said input drive shaft and extends between said nose and an inner wall of said output drive shaft that defines said output drive shaft bore.

21. The drill attachment of claim 17, wherein: said housing is a multi-part assembly having an input housing and output housing; said input drive shaft is rotatably mounted in said input housing; and said output drive shaft is rotatably mounted to said output housing.

22. The drill attachment of claim 17, wherein said ring gear has a single set of teeth and both said input planet gears and said output planet gears engage the single set of teeth of said ring gear.

* * * * *